United States Patent [19]

Oberheim et al.

[11] Patent Number: 4,815,847

[45] Date of Patent: Mar. 28, 1989

[54] PROCESS AND DEVICE FOR THE GENERATION OF A LINEARLY DEPENDENT MEASUREMENT SIGNAL

[75] Inventors: Wolfgang Oberheim, Pohlheim, Fed. Rep. of Germany; Tetsuo Hadeishi, Kensington, Calif.

[73] Assignee: Gruen Optik Wetzlar GmbH, Wetzlar, Fed. Rep. of Germany

[21] Appl. No.: 23,497

[22] Filed: Mar. 9, 1987

[30] Foreign Application Priority Data

Mar. 8, 1986 [DE] Fed. Rep. of Germany ....... 3607658

[51] Int. Cl.$^4$ .......................... G01J 3/36; G01N 21/72
[52] U.S. Cl. .................................... 356/307; 356/315; 356/312; 356/319
[58] Field of Search ................ 356/307, 308, 310, 326, 356/328, 315, 319

[56] References Cited

U.S. PATENT DOCUMENTS

| | | | |
|---|---|---|---|
| 3,586,441 | 6/1971 | Smith et al. | 356/315 X |
| 3,689,158 | 9/1972 | Shifrin | 356/307 X |
| 3,937,577 | 2/1976 | Dorsch | 356/312 |
| 4,035,083 | 7/1977 | Woodriff et al. | 356/307 X |

OTHER PUBLICATIONS

"Nachrichten aus Chemie, Technik und Laboratorium" (Reports from the Chemical, Engineering and Laboratory Sectors), Zeeman-Atom-Absorptions-Spektroskopie, vol. 29, No. 12/81 (1981).

Primary Examiner—Vincent P. McGraw
Attorney, Agent, or Firm—Foley & Lardner, Schwartz, Jeffery Schwaab, Mack, Blumenthal & Evans

[57] ABSTRACT

A process which extends the measurement range of Zeeman atomic absorption spectroscopy by linearization of the calibration curve in the region of relatively high sample concentration. The intensities of the Zeeman components $I\pi o$, $I\sigma o$, $I\pi$ and $I\sigma$ are measured before entry into the measurement cell and after absorption by the measurement sample and are associated according to the formula $$\left[ \ln \frac{I\pi}{I\pi o} - \ln \frac{I\sigma}{I\sigma o} \right]$$

or $$\left[ \ln \frac{I\pi}{I\sigma} - \ln \frac{I\pi o}{I\sigma o} \right].$$

5 Claims, 2 Drawing Sheets

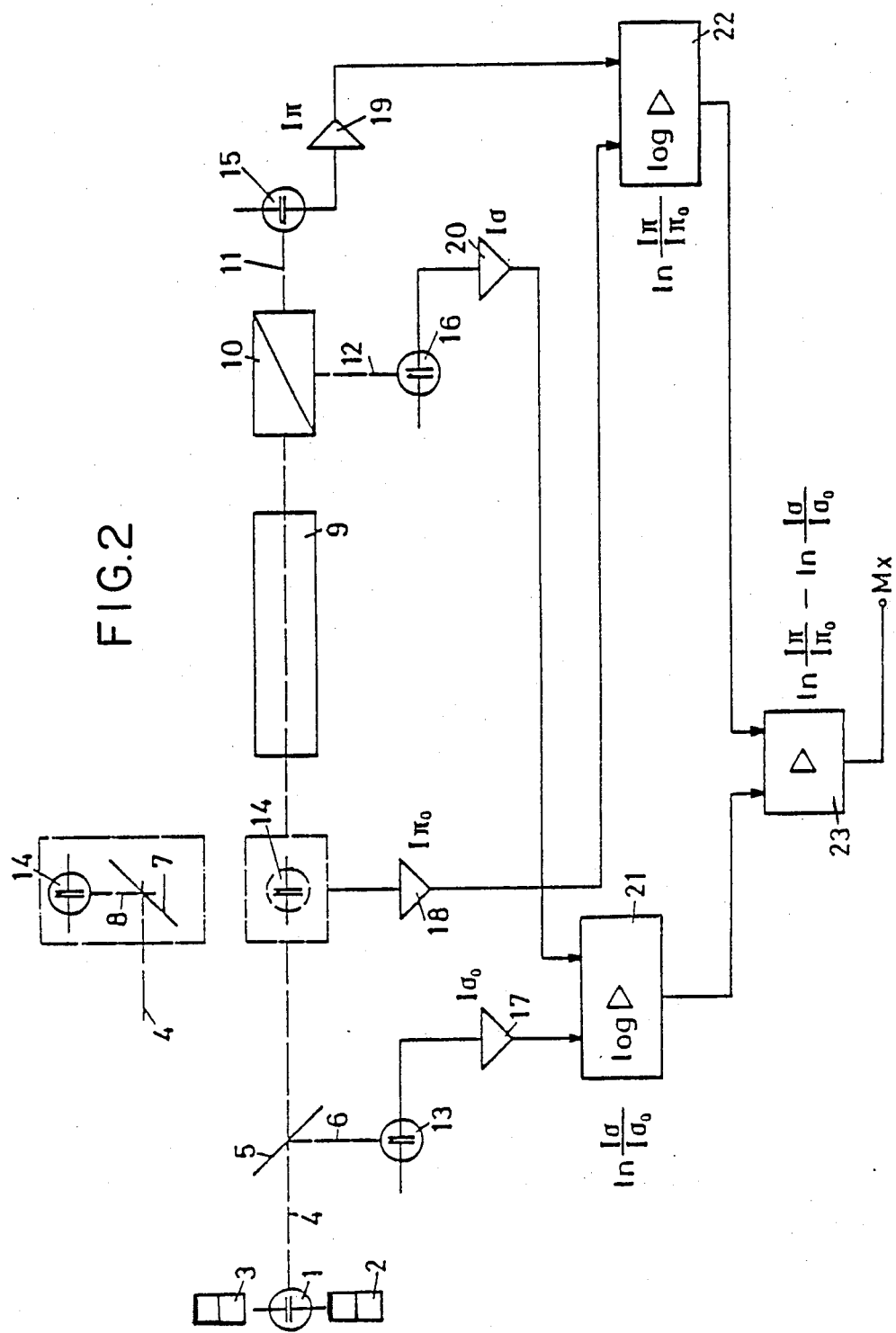

PROCESS AND DEVICE FOR THE GENERATION OF A LINEARLY DEPENDENT MEASUREMENT SIGNAL

BACKGROUND OF THE INVENTION

The invention relates to a process and a device for the generation of a measurement signal Mx, which is a linear function of the numerical density Nx of absorbing atoms or molecules in a sample volume, with a Zeeman atomic absorption spectometer, in which the spectral lamp generating the measurement beam is disposed in a magnetic field.

Various processes of Zeeman atomic absorption spectroscopy (ZAAS) are known. A brief survey of the processes which are used in practice can be found in "Nachrichten aus Chemie, Technik und Laboratorium" (Reports from the Chemical, Engineering and Laboratory Sectors), volume 29, No. 12/81. The invention is concerned with direct ZAAS, in which the emission line is split into the two polarization components $\pi$ and $\sigma$. The $\pi$ component is employed to measure the atomic absorption and the background absorption, and the $\sigma$ component is employed to measure only the background absorption closely adjacent to the atomic absorption. The pure atomic absorption measurement signal is thus obtained by difference formation.

In the known measuring arrangements, the difference of the transmitted intensities $I\pi$ and $I\sigma$ is used as the measurement signal. It is known that the difference signal is an approximately linear function of the number of absorbing atoms or molecules only up to a specific sample concentration. After reaching a maximum, the difference signal decreases again if there is a further increase in the sample concentration.

This phenomenon is described as the "roll-over effect" of the measurement curve and is explained by a more or less intense specific absorption of the $\sigma$ component as well.

For both components $\pi$ and $\sigma$, the transmitted intensity is a function of the irradiated intensity Io and the absorption coefficient $\alpha$, according to the absorption law $I = Io \cdot e^{-\alpha \cdot d}$. The absorption coefficient is proportional to the numerical density N of the absorbing atoms (or molecules), and "d" is the thickness of the absorbing layer. If the layer thickness and absorption constant are now combined, then for the two transmitted intensities the result is $I\pi = I\pi o \cdot e^{-a\pi \cdot N}$ and $I\sigma = I\sigma o \cdot e^{-a\sigma \cdot N}$.

For the measuring arrangements which are customarily employed, it can be assumed that $I\sigma o - I\pi o = Io$ and $a\pi > a\sigma$. If N is now varied from $0 \to \infty$, then this results in measurement curves for $I\pi$ (N) and $I\sigma$ (N) which commence at Io and tend towards 0 in the form of an e function as N becomes greater. In the known measuring arrangements, the difference of the transmitted intensities $(I\pi - I\sigma)$ is evaluated as the measurement signal. This measurement signal commences at 0 $(I\sigma o - I\pi o = 0)$, then increases with increasing N because $a\pi > a\sigma$, and then again tends towards 0, since both $I\pi$ and also $I\sigma$ tend towards 0 as $N \to \infty$.

The object of the invention is to provide a process and a suitable measuring device which are suitable to expand the measurement range of ZAAS by linearization of the calibration curve into the region of higher sample concentrations.

SUMMARY OF THE INVENTION

The essential difference of the novel process, as compared with the known processes, consists in that the signal evaluation is no longer based on the directly recorded difference signal of the $\pi$ and $\sigma$ absorption, but on the difference of ratio values, expressed in logarithmic form, for the individual measurement beam components. The process is based on the consideration that for each irradiated wavelength $\lambda$ or each irradiated light frequency $\nu$, the absorption law is applicable in the form:

$$I(\nu) = Io(\nu)e^{-a(\nu) \cdot d \cdot N}.$$

where is the measured light intensity after passing through the sample, $Io(\nu)$ is the incident light intensity, $a(\nu)$ is the absorption constant dependent upon the sample, "d" is the thickness of the sample through which the radiation passes, and N is the numerical density of the absorbing atoms or molecules. In the course of the further considerations, the existing dependence upon the light frequency is to be disregarded and "c" is to be inserted for the absorption coefficient $a(\nu) \cdot d$.

Since, in ZAAS, the incident light consists of two components $\pi$ and $\sigma$, which possess the same wavelength but mutually perpendicular polarization, the absorption law gives the following:

$$I\pi = I\pi o \cdot e^{-c\pi \cdot N} \qquad (1)$$

$$I\sigma = I\sigma o \cdot e^{-c\sigma \cdot N} \qquad (2)$$

$I\pi o$, $I\sigma o$, $I\pi$ and $I\sigma$ are determined by direct measurement. There are then two possibilities for solving the system of equations, in order to determine the constants $c\pi$ and $c\sigma$.

The first method consists in dividing equation (1) by equation (2) and thereafter expressing the result in logarithmic form. The second method consists in dividing equation (1) and equation (2) in each case by the intensity factor on the right-hand side, then expressing each one of the equations initially in logarithmic form, and thereafter subtracting the two equations from one another.

Method 1 gives the following:

$$M = \ln \frac{I\pi}{I\sigma} - \ln \frac{I\pi o}{I\sigma o} = (c\sigma - c\pi) \cdot N + (\ln c1 - \ln c2) \qquad (3)$$

Method 2 gives the following:

$$M = \ln \frac{I\pi}{I\pi o} - \ln \frac{I\sigma}{I\sigma o} = (c\sigma - c\pi) \cdot N + (\ln c3 - \ln c4) \qquad (4)$$

The association, as described, of the four directly obtained measurement signals thus gives a derived measurement signal M of the form $$M = A \cdot N + B \qquad (5)$$

In this expression, B is a correction constant, which also takes account of the fact that the intensity ratios on the left-hand side can differ from the ratio 1:1 as a result of geometric errors, differing sensitivity of the detectors, etc. Since the intensity ratios are expressed in logarithmic form, there is an additive correction. The only prerequisite with the above considerations is that the detectors are driven in a range in which a linear interrelationship is present between the intensity and the measured quantity.

The correction constant B can be determined in each instance by a measurement without a sample in the system. In these circumstances, $N=0$, and the result is $B=Mo$.

The constant A takes account of the differing absorption behavior of the sample for the $\pi$ and $\sigma$ components of the measurement beam. It can be determined by a calibration measurement with a known sample concentration Nc, and emerges as follows:

$$A = \frac{Mc - Mo}{Nc}$$

Equation (5) shows that, in the entire range in which the detectors exhibit linear behavior, the measurement signal M is likewise a linear function of the sample concentration. With regard to the constants A and B which are to be determined for the measuring arrangement and the sample to be investigated respectively, the result is thus a measurement signal Mx of the form $$Mx = \frac{Mc - Mo}{Nc} \cdot Nx + Mo \quad (6)$$

BRIEF DESCRIPTION OF THE DRAWINGS

Exemplary embodiments for carrying out the process according to the invention are shown in the drawings, in which:

FIG. 2 shows a block diagram of the apparatus for carrying out the invention in accordance with a second embodiment thereof.

DETAILED DESCRIPTION OF THE PREFERRED EMBODIMENTS

Figure 1:
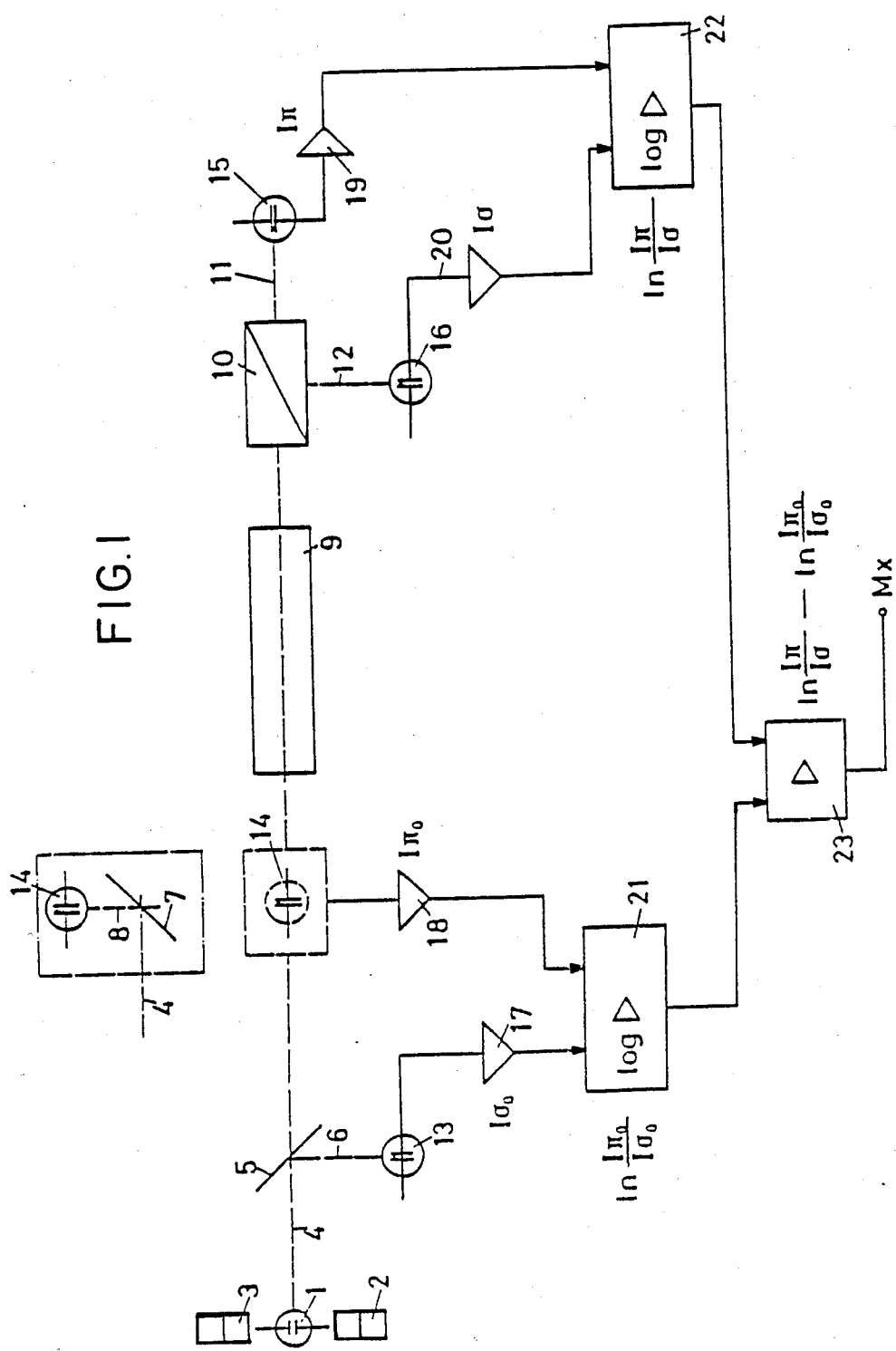
FIG. 1 shows a block diagram of the apparatus for carrying out the invention in accordance with a first embodiment thereof.

In FIG. 1, an atomic spectral lamp 1 is situated between the poles 2, 3 of a magnet. Both are excited, by circuit means which are known per se and which are not further represented, to emit a measurement beam 4, which includes the two Zeeman components $\pi$ and $\sigma$.

By means of a first quartz plate 5, which is arranged at 45° to the measurement beam, a first partial beam 6 is isolated, which is intended to contain the $\sigma$ component, on account of the polarization properties of the quartz plate 5. By means of a second quartz plate 7, which is oriented in such a manner that it isolates a second partial beam 8 in a plane which is perpendicular to the plane of the drawing, a part of the $\pi$ component is isolated.

It is also possible, in the first instance, to isolate a partial beam from the measurement beam by means of a neutral divider and then to split this into the $\pi$ and $\sigma$ components by means of polarizing elements The arrangement can also include a plurality of spectral lamps, the emission of which can be combined into a common measurement beam. Furthermore, the quartz plates 5 and 7 can be replaced by similarly-acting polarizing divider combinations with polarizing filter layers.

The measurement beam 4 then pulses through a measurement cell 9, which can be, for example, a graphite tube furnace. The radiation which is not absorbed by the sample is split again, by means of a polarizing divider 10, into two partial beams 11, 12, which include in each instance only the $\pi$ component or the $\sigma$ component.

Behind the four partial beams 6, 8, 11, 12 there are disposed photoelectric detectors 13, 14, 15, 16, which emit the four individual measurement signals $I\sigma o$, $I\pi o$, $I\pi$, $I\sigma$, which are further amplified in amplifiers 17, 18, 19, 20 for the further signal processing.

The output signals of the amplifiers 17, 18 are fed to a computing circuit 21, in which, from the two signals, the ratio is formed and expressed in logarithmic form. The same signal processing takes place in a computing circuit 22 with the output signals of the amplifiers 19, 20. The computing circuits 21, 22 are then connected to a difference former 23, at the output of which the desired measurement signal Mx appears. When the measurement cell 9 is empty, the apparatus constant $B = M_o$ can be picked off here, and, in the case of the calibration measurement with a known sample concentration, the signal Mc. Both can be stored in a following evaluation unit, which is not further represented, and associated with the measurement signals Mx in accordance with equation (6).

The arrangement shown in FIG. 2 is in conformity, in all functional units, with those described in FIG. 1. The difference consists in that in this instance the output signals of the amplifiers 17, 20 and 18, 19 are fed in each instance to the computing circuits 21, 22. The measurement signal is accordingly obtained in accordance with method 2.

What is claimed is:

1. A process for the generation of a measurement signal, which is a linear function of the numerical density Nx of absorbing atoms or molecules in a sample volume, with a Zeeman atomic absorption spectrometer, in which the spectral lamp generating the measurement beam is disposed in a magnetic field, comprising the steps of:

(a) splitting the measurement beam in the magnetic field into Zeeman components $\pi$ and $\sigma$;

(b) isolating partial beams from the measurement beam before entry into the sample volume and measuring the intensities $I\pi o$ and $I\sigma o$ of the Zeeman components from said partial beams;

(c) after passage of the measurement beam through the sample volume measuring from said measurement beam the intensities $I\pi$ and $I\sigma$ of the Zeeman components;

(d) generating a measurement signal from the measured intensities $I\pi o$, $I\sigma o$, $I\pi$ and $I\sigma$ according to one of the following formulas (1) and (2):

$$\left[ \ln \frac{I\pi}{I\pi o} - \ln \frac{I\sigma}{I\sigma o} \right] \quad (1)$$

or $$\left[ \ln \frac{I\pi}{I\sigma} - \ln \frac{I\pi o}{I\sigma o} \right] \quad (2)$$

2. A process as recited in claim 1 wherein said measurement signal is Mx defined as $$Mx = \frac{Mc - Mo}{Nc} \cdot Nx + Mo$$

and said process further includes the steps of, performing steps (a)–(d) without a sample in the sample volume wherein the resulting measurement signal is defined as Mo and performing steps (a)–(d) with a sample of known numerical density wherein the resulting measurement signal is defined as Mc.

3. A measuring device for the generation of a measurement signal Mx, which is a linear function of the numerical density Nx of absorbing atoms or molecules in a sample volume, with a Zeeman atomic absorption spectrometer, in which the spectral lamp generating the measurement beam is disposed in a magnetic field, comprising:

(a) first means, disposed in a path of the measurement beam prior to said sample volume for isolating partial beams of $\pi$ and $\sigma$ polarization components generated by the magnetic field;

(b) second means, disposed after the measurement beam passes through said sample volume for splitting the measurement beam into partial beams of $\pi$ and $\sigma$ polarization components;

(c) a photoelectric detector, associated with each of the partial beams, for generating a signal as a function of the intensity of each associated partial beam;

(d) circuit means for generating logarithmic ratio signals formed as a logarithmic ratio for pairs of said intensity signals; and (e) a difference circuit connected to receive said logarithmic ratio signals for generating an output signal Mx which is a linear function of the numerical density Nx in the sample volume.

4. A measuring device as recited in claim 3, wherein said circuit means includes:

(a) first circuit means for generating a signal proportional to $\ln(I\pi o/I\sigma o)$ where $I\pi o$ and $I\sigma o$ are the intensity signals corresponding to the partial beams of said first means, and (b) second circuit means for generating a signal proportional to $\ln(I\pi/I\sigma)$ where $I\pi$ and $I\sigma$ are the intensity signals corresponding to the partial beams of said second means, and wherein said difference circuit generates Mx defined as $$Mx = \ln \frac{I\pi}{I\sigma} - \ln \frac{I\pi o}{I\sigma o}$$

5. A measuring device as recited in claim 3, wherein said circuit means includes:

(a) first circuit means for generating a signal proportional to $\ln(I\sigma/I\sigma o)$ where $I\sigma o$ and $I\sigma$ are the intensity signals of the $\sigma$ components corresponding to the partial beams of said first and second means respectively, and (b) second circuit means for generating a signal proportional to $\ln(I\pi/I\pi o)$ where $I\pi o$ and $I\pi$ are the intensity signals of the $\pi$ components corresponding to the partial beams of said first and second means respectively, and wherein said difference circuit generates Mx defined as $$Mx = \ln \frac{I\pi}{I\pi o} - \ln \frac{I\sigma}{I\sigma o}$$

* * * * *